United States Patent [19]

Schach et al.

[11] Patent Number: 5,466,859
[45] Date of Patent: Nov. 14, 1995

[54] PROCESS FOR PREPARING FLUOROBENZONITRILES

[75] Inventors: Thomas Schach, Gernsheim; Theodor Papenfuhs, Frankfurt am Main; Ralf Pfirmann, Griesheim, all of Germany

[73] Assignee: Hoechst Aktiengesellschaft, Frankfurt, Germany

[21] Appl. No.: 277,518

[22] Filed: Jul. 19, 1994

[30] Foreign Application Priority Data

Jul. 21, 1993 [DE]  Germany ............................ 43 24 368.1

[51] Int. Cl.⁶ ................................................. C07C 253/30
[52] U.S. Cl. ........................................................ 558/425
[58] Field of Search ............................................ 558/425

[56] References Cited

U.S. PATENT DOCUMENTS

| | | | |
|---|---|---|---|
| 4,351,777 | 9/1982 | Ramanadin et al. | 558/425 |
| 4,952,719 | 8/1990 | Maul et al. | 558/425 |
| 4,978,769 | 12/1990 | Kysela et al. | 558/425 X |
| 5,153,350 | 10/1992 | Braish | 558/425 X |
| 5,237,087 | 8/1993 | Clark et al. | 558/425 |

FOREIGN PATENT DOCUMENTS

| | | | |
|---|---|---|---|
| 0497239 | 8/1992 | European Pat. Off. | 558/425 |
| 0222463 | 12/1984 | Japan | 558/425 |
| 0072850 | 4/1985 | Japan | 558/425 |
| 0072851 | 4/1985 | Japan | 558/425 |
| 0184057 | 9/1985 | Japan | 558/425 |

*Primary Examiner*—Joseph Paul Brust
*Attorney, Agent, or Firm*—Connolly and Hutz

[57] ABSTRACT

Fluorobenzonitriles and chlorofluorobenzonitriles are prepared in an advantageous manner from the corresponding chlorobenzonitriles and an alkali metal fluoride in a chlorine-fluorine exchange reaction, by catalyzing the reaction with a quaternary ammonium compound comprising at least one alkoxypolyoxyalkyl radical.

18 Claims, No Drawings

PROCESS FOR PREPARING FLUOROBENZONITRILES

The present invention relates to an improved process for preparing fluorobenzonitriles by reaction of the corresponding chlorobenzonitriles with alkali metal fluorides in the presence of a novel catalyst system. Halogen exchange, preferably that of activated chlorobenzonitriles, is a customary method for introducing fluoro-substituents into an aromatic system. In general, the reaction is carried out in the presence of aprotic dipolar solvents and alkali metal fluorides as fluoride source (U.S. Pat. No. 4,226,811). Prominent disadvantages of these processes are the high reaction temperatures, moderate product yields and long reaction times.

As an alternative, use can be made of conventional phase transfer catalysts which enable some of the above-described disadvantages to be improved. Other problems such as, for example, poor stirrability of the reaction suspension in solvent-free processes remain. The phase transfer catalysts used hitherto have been quaternary alkylammonium or alkylphosphonium salts (U.S. Pat. No. 4,287,374), pyridinium salts (WO 87/04149) or crown ethers which sometimes have only low reactivities or are only moderately stable at the reaction temperatures required.

Multiple chlorine-fluorine exchange reactions without solvent have hitherto been possible only with limitations. The high salt content of the reaction suspension generally led to non-stirrable systems which lead, even under the most favorable conditions, only to low conversions and yields. Hitherto, a double Cl/F exchange has only been successful in the presence of suitable solvents such as, for example, sulfolane or dimethyl sulfoxide (U.S. Pat. No. 4,209,457). EP-A-0 049 186 describes a process for preparing fluorobenzonitriles in the presence of a tertiary polyetheramine and sulfolane, in which, however, temperatures between 180° and 250° C. are required.

In view of these limitations and disadvantages there was a great need for an improved process with which the disadvantages inherent in the known processes are avoided and good to very good yields, lower reaction temperatures and shortened reaction times are made possible and smaller amounts of polymeric decomposition products are obtained. Particular importance has been attached, in particular, to coping with stirring problems and workup problems in solvent-free processes and in processes having only very small amounts of solvent.

It has been found that fluorobenzonitriles and chlorofluorobenzonitriles can be advantageously prepared by reacting the corresponding chlorobenzonitriles with alkali metal fluorides in the presence of a quaternary ammonium compound comprising at least one alkoxypolyoxyalkyl radical.

The present invention provides a process for preparing fluorobenzonitriles by reaction of a compound of the formula (4)

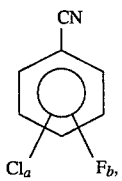

(4)

in which
a is an integer from 1 to 5 and
b is a number from 0 to 3,
with an alkali metal fluoride in the presence of a catalyst, wherein the catalyst consists essentially of a) one or more quaternary ammonium compound(s) of the formula (1)

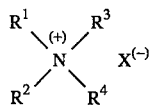

(1)

in which $R^1$, $R^2$ and $R^3$ are identical or different and are a linear or branched alkoxypolyoxyalkyl radical of the formula —$(C_mH_{2m}O)_pR^5$, in which $R^5$ is hydrogen or a linear or branched alkyl radical having from 1 to 16, preferably from 1 to 8, carbon atoms, m is an integer from 1 to 10, preferably from 1 to 5, and p is a number from 1 to 15, preferably from 2 to 10; or
a linear or branched alkyl radical having from 1 to 30, preferably from 1 to 18, carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;

$R^4$ is a linear or branched alkoxypolyoxyalkyl radical of the formula —$(C_mH_{2m}O)_pR^5$; and $X^e$ is an inorganic anion, preferably fluoride, chloride, bromide, $SO_4^{2-}/2$ or hydrogen sulfate;

or of a mixture of the component a) and b) one or more quaternary ammonium salt(s) or phosphonium salt(s) of the formula (2)

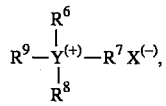

(2)

in which $R^6$, $R^7$, $R^8$ and $R^9$ are identical or different and are a linear or branched alkyl radical having from 1 to 22, preferably from 1 to 16, carbon atoms; or an unsubstituted or substituted aryl radical or a $C_1$–$C_4$-alkylaryl radical, with aryl being phenyl or naphthyl and said substituents being halogen, $C_1$–$C_4$-alkyl, $C_1$–$C_4$-alkoxy, nitro or cyano; and Y is N or P;

or of a mixture of the component a) and c) one or more polyether(s) of the formula (3)

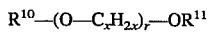

$R^{10}$—$(O—C_xH_{2x})_r$—$OR^{11}$ (3), in which $R^{10}$ and $R^{11}$ are identical or different and are hydrogen or a linear or branched alkyl radical having from 1 to 16, preferably from 1 to 8, carbon atoms, x is an integer from 2 to 6, preferably 2 or 3, and r is a number from 0 to 20, preferably from 4 to 14;

or a crown ether;

or of a mixture of the components a), b) and c).

The catalyst preferably consists exclusively of component a), however it can be advantageous to use a mixture of the components a) and b) or of the components a) and c) or of the components a), b) and c). In the case of a simple chlorine-fluorine exchange, i.e. if only one chlorine atom is to be replaced by a fluorine atom, it is often advantageous to use a mixture of components a) and b). In the case of a multiple chlorine-fluorine exchange, i.e. if two or more chlorine atoms are to be replaced by fluorine atoms, it is often advantageous to use a mixture of components a) and c) or of a), b) and c).

The mixing ratios of the components a) and b), a) and c) and also a), b) and c) can vary within a wide range, with the proviso that the component a) makes up at least 5% by weight, preferably from 20 to 80% by weight, of the total catalyst.

In the linear or branched alkoxypolyoxyalkyl radical of the formula $-(C_mH_{2m}O)_pR^5$ present in the compound of the formula (1), identical or different alkoxy units can be linked to one another.

The number of the linear or branched alkoxypolyoxyalkyl radicals present in the compound of the formula (1) is preferably one or two. For the purposes of the present invention, particularly preferred compounds of the formula (1) are dimethyl-di(ethoxypolyoxypropyl)ammonium chloride, dimethyldi(ethoxypolyoxypropyl methyl ether)ammonium chloride, dimethyl(ethoxypolyoxypropyl)(ethoxypolyoxypropyl methyl ether)ammonium chloride, dimethyldi(ethoxypolyoxyethyl)ammonium chloride, dimethyldi(ethoxypolyoxyethyl methyl ether)ammonium chloride, dimethyl(ethoxypolyoxyethyl)(ethoxypolyoxyethyl methyl ether)ammonium chloride, in each case having a mean chain length p of 3, furthermore trimethyl(ethoxypolyoxypropyl)ammonium chloride and trimethyl(ethoxypolyoxypropyl methyl ether)ammonium chloride, in each case having a mean chain length p of 8, or a mixture of the specified compounds.

The described compounds of the formula (1) can be prepared in a known manner (U.S. Pat. No. 3,123,641, U.S. Pat. No. 3,141,905) from the corresponding ethanolamines which, after reaction with alkylene oxides and subsequent quaternization with or without simultaneous etherification, give the desired compounds in good yields.

For the purposes of the present invention, preferred compounds of the formula (2) are octadecyltrimethylammonium chloride, distearyldimethylammonium chloride, tetramethylammonium chloride, tetramethylammonium bromide, hexadecyltrimethylammonium chloride, benzyltrimethylammonium chloride, hexadecyltributylphosphonium bromide, stearyltributylphosphonium bromide, tetrabutylphosphonium chloride, tetrabutylphosphonium bromide and tetraoctylphosphonium bromide.

For the purposes of the present invention, preferred polyethers of the formula (3) possess a mean molecular mass between 300 and 800. Particular preference is given to a mixture of polyethylene glycol dimethyl ethers having chain lengths r of from 6 to 17 and a mean molecular mass of 500. In place of or in combination with polyethers of the formula (3), customary crown ethers, for example 18-crown-6, can also be used.

Suitable starting compounds of the formula (4) for the process of the invention are:

monochlorobenzonitriles such as, for example, 2-chlorobenzonitrile and 4-chlorobenzonitrile; dichlorobenzonitriles such as, for example, 2,3-dichlorobenzonitrile, 3,4-dichlorobenzonitrile, 2,5-dichlorobenzonitrile, 4-chloro-3-fluorobenzonitrile, 2-chloro-5-fluorobenzonitrile, 2,4-dichlorobenzonitrile, 2,6-dichlorobenzonitrile, 2,4-dichloro-3-fluorobenzonitrile and 2,4-dichloro-5-fluorobenzonitrile; trichlorobenzonitriles such as, for example, 2,4,5-trichlorobenzonitrile, 2,3,4-trichlorobenzonitrile, 2,3,4-trichloro-5-fluorobenzonitrile and 2,4,5-trichloro-3-fluorobenzonitrile.

By means of the process of the invention, one, two or three, preferably one or two, chlorine atoms in the specified starting compounds can be replaced by fluorine atoms, so that the end products obtained are, for example: monofluorobenzonitriles such as, for example, 2-fluorobenzonitrile and 4-fluorobenzonitrile; chlorofluorobenzonitriles such as, for example, 3-chloro-2-fluorobenzonitrile, 3-chloro-4-fluorobenzonitrile and 5-chloro-2-fluorobenzonitrile; difluorobenzonitriles such as, for example, 3,4-difluorobenzonitrile, 2,5-difluorobenzonitrile, 2,4-difluorobenzonitrile, 2,6-difluorobenzonitrile, 5-chloro-2,4-difluorobenzonitrile and 3-chloro-2,4-difluorobenzonitrile; trifluorobenzonitriles such as, for example, 2,3,4-trifluorobenzonitrile, 2,4,5-trifluorobenzonitrile, 3-chloro-2,4,5-trifluorobenzonitrile and 5-chloro-2,3,4-trifluorobenzonitrile.

The alkali metal fluorides used are preferably potassium fluoride, rubidium fluoride or cesium fluoride or combinations of these, in particular potassium fluoride. It is an advantage of the process of the invention that the alkali metal fluorides used can have a water content of up to 3%. This makes it possible, for example, to use technical grade potassium fluoride without pretreatment.

In the process of the invention, the catalyst is advantageously used in amounts of from 1 to 35% by weight, preferably from 10 to 25% by weight, based on the aromatic starting compound. The molar ratio of catalyst to starting compound is here equal to or less than 1:8, preferably from 1:10 to 1:50.

As regards the molar ratio of the alkali metal fluoride to the starting compound, use is advantageously made of from 60 to 200 mol %, preferably from 100 to 140 mol %, based on each chlorine atom to be replaced, of alkali metal fluoride.

Double or multiple chlorine-fluorine exchange reactions for preparing fluorobenzonitriles have hitherto only been possible in the presence of solvents. The high salt content of the reaction suspension generally led to non-stirrable systems which led, even under the most favorable conditions, to only small conversions and yields. In the process of the invention, even at very high salt contents in the reaction suspension, there are now no stirring problems, so that even double or multiple exchange reactions can usually be carried out without problems in the absence of solvent. Finally, the simultaneously significantly lower reaction temperatures in comparison with the prior art, together with the good stirrability of the reaction suspension, lead to a significant increase in the yield and a reduction in secondary reactions.

While temperatures of from 200° C. to over 300° C. were hitherto required for chlorine-fluorine exchange reactions, the reaction temperatures of the process of the invention are from 80° to 220° C. preferably from 90° to 180° C., in particular from 120° to 170° C.

The process of the invention can be carried out in the presence or absence of solvents. If solvents are used, aprotic and dipolar aprotic and also protic solvents are suitable. Suitable dipolar aprotic solvents are, for example, dimethyl sulfoxide, dimethyl sulfone, sulfolane, dimethylformamide, dimethylacetamide, 1,3-dimethylimidazolin-2-one, acetonitrile and benzonitrile. Suitable aprotic solvents without prominent dipolar character are, for example, benzene, toluene, xylene, chlorotoluenes, chlorobenzene and dichlorobenzenes. The use of protic solvents such as, for example, alcohols, is likewise possible. Protic solvents used are methanol, ethanol, propanol, butanol, i-propanol or polyalkylene glycols having ethylene, propylene or butylene units.

The aprotic or dipolar aprotic solvent can be used in any amounts, however preference is given to small amounts in the range from 5 to 30% by weight, based on the aromatics used. When using protic solvents, the amounts used lie in the range from 0.1 to 5% by weight, preferably from 0.1 to 2% by weight, based on the aromatic used.

The catalyst of the invention can be used at atmospheric pressure and also at superatmospheric or subatmospheric pressure. These properties are utilized, for example, by adding small amounts of a low-boiling aprotic solvent which forms an azeotrope with water, such as, for example, benzene, xylene, mesitylene or toluene, to the reaction suspension prior to the start of the reaction. Subsequently, a part of the solvent is again removed together with water from the reaction suspension by application of a vacuum. This process procedure enables the reaction rate and the yield to be increased and the formation of byproducts to be minimized.

The process of the invention can be carried out in the presence or absence of atmospheric oxygen; it is preferably carried out under protective gas such as, for example, argon or nitrogen. In the process of the invention, it is to be ensured that the reaction mixture is well mixed during the whole reaction.

Fluorobenzonitriles are important as intermediates in the field of crop protection and as synthetic building blocks for pharmaceuticals and dyes.

The following examples illustrate the process of the invention, without limiting it to them. For the purposes of the present invention, "polyethylene glycol dimethyl ether 500" is the said polyether having a mean molecular mass of about 500. The trimethyl(ethoxypolyoxypropyl)ammonium chloride used in the examples has a mean chain length p of 8 and was used as a product having a purity of from 84 to 89% by weight. This product also comprises from 10 to 13% by weight of free polypropylene glycol and up to 2% by weight of water. The dimethyldi(ethoxypolyoxypropyl)ammonium chloride used has a mean chain length p of 3 and is a product having a purity of from 90 to 95% by weight, also comprising from 5 to 10% by weight of polypropylene glycol and about 0.2% by weight of water.

If the two catalysts were used as etherified compounds, the polypropylene glycols were likewise in etherified form. The degree of etherification was 86% in the case of dimethoxydi(ethoxypolyoxypropyl methyl ether)ammonium chloride. The course of the reaction over time was followed by gas chromatographic analysis (GC) and the amount of the desired product present in the reaction mixture in each case was given in the form of GC percentage areas.

EXAMPLE 1

2,4,5-Trifluorobenzonitrile

In a 100 ml flange flask fitted with a distillation bridge and anchor stirrer, 58.1 g (1 mol) of potassium fluoride, 9.5 g (0.017 mol) of dimethyldi(ethoxypolyoxypropyl methyl ether)ammonium chloride and 12.4 g (0.025 mol) of polyethylene glycol-dimethyl ether 500 were introduced at 100° C. into the melt of 95.0 g (0.5 mol) of 2,4-dichloro-5-fluorobenzonitrile. Subsequently, 20 g (0.18 mol) of xylene were added and the reaction suspension was azeotropically dried by application of a vacuum of 20 mbar and heating to 120° C. After the xylene had been distilled off, the reaction suspension was heated to 150° C. and stirred for 21 hours at this temperature. Amount of 2,4,5-trifluorobenzonitrile formed:

after 4 hours: 5 GC area-% after 21 hours: 15 GC area-%.

In addition, the following amounts of 2-chloro-4,5-difluorobenzonitrile were formed:

after 2 hours: 52 GC area-% after 4 hours: 70 GC area-%.

EXAMPLE 2

2-Chloro-4,5-difluorobenzonitrile

In a 100 ml flange flask fitted with a distillation bridge and anchor stirrer, 14.5 g (0.25 mol) of potassium fluoride, 4.8 g (0.007 mol) of trimethyl(ethoxypolyoxypropyl)ammonium chloride, 6.2 g (0.012 mol) of polyethylene glycol dimethyl ether 500 and 2.4 g (0.007 mol) of tetrabutylphosphonium bromide were introduced at 100° C. into the melt of 47.5 g (0.25 mol) of 2,4-dichloro-5-fluorobenzonitrile. Subsequently, 10 g (0.09 mol) of xylene were added and the reaction suspension was azeotropically dried by application of a vacuum of 20 mbar and heating to 130° C. After the xylene had been distilled off, the reaction suspension was heated to 140° C. and stirred for 8 hours at this temperature. Amount of 2-chloro-4,5-difluorobenzonitrile formed:

after 2 hours: 50 GC area-% after 8 hours: 70 GC area-%.

EXAMPLE 3

2,6-Difluorobenzonitrile

In a 500 ml flange flask fitted with a distillation bridge and anchor stirrer, 127.8 g (2.2 mol) of potassium fluoride and 50.3 g (0.07 mol) of trimethyl(ethoxypolyoxypropyl)ammonium chloride were introduced at 100° C. into the melt of 172.0 g (1.0 mol) of 2,6-dichlorobenzonitrile. Subsequently, 60 g (0.57 mol) of xylene were added and the reaction suspension was azeotropically dried by application of a vacuum of 20 mbar and heating to 130° C. The reaction suspension was heated to 180° C. and stirred for 16 hours at this temperature. Amount of 2,6-difluorobenzonitrile formed:

after 10 hours: 52 GC area-% after 16 hours: 69 GC area-%.

In addition, the following amounts of 2-chloro-6-fluorobenzonitrile were formed:

after 2 hours: 46 GC area-% after 10 hours: 29 GC area-%.

EXAMPLE 4

2,6-difluorobenzonitrile

In a 500 ml flange flask and fitted with a distillation bridge and anchor stirrer, 127.8 g (2.2 mol) of potassium fluoride and 25.0 g (0.05 mol) of dimethyldi(ethoxypolyoxypropyl)ammonium chloride were introduced at 100 ° C. into the melt of 172.0 g (1.0 mol) of 2,6-dichlorobenzonitrile.

Subsequently, 60 g (0.57 mol) of xylene were added and the reaction suspension was azeotropically dried by application of a vacuum of 20 mbar and heating to 130° C. The reaction suspension was heated to 180° C. and stirred for 44 hours at this temperature. Amount of 2,6-difluorobenzonitrile formed:

after 20 hours: 39 GC area-% after 44 hours: 83 GC area-%.

The isolated yield of 2,6-difluorobenzonitrile was 80% of theory.

We claim:

1. A process for replacement, with fluorine, of at least one chlorine atom of a compound of the formula (4)

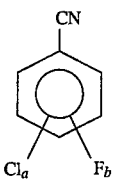 (4)

in which
- a is a number from 1 to 5 and
- b is a number from 0 to 3, said process comprising
reacting said compound of formula (4) with an alkali metal fluoride at a reaction temperature in the range of from 80 to 220° C. in the presence of:
(1) 0 to 30% by weight aprotic or 0 to 5% by weight of a protic solvent, based on the weight of said compound of formula (4),
(2) from 1 to 35% by weight, based on the weight of the compound of formula (4), of a catalyst, said catalyst comprising at least 5% by weight, based on the total catalyst, of a quaternary ammonium compound of the formula (1)

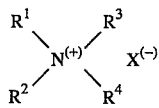 (1)

in which
- $R^4$ is a linear or branched alkoxypolyoxyalkyl radical of the formula $(C_mH_{2m}O)_pR^5$, in which $R^5$ is a hydrogen or a linear or branched alkyl radical having from 1 to 16 carbon atoms, m is a number from 1 to 10, and p is a number from 1 to 15;
- $R^1$, $R^2$, and $R^3$ are the same or different and are: a linear or branched alkoxypolyoxyalkyl radical of the formula $(C_mH_{2m}O)_pR^5$, in which $R^5$, m, and p are as previously defined; a linear or branched alkyl radical having from 1 to 30 carbon atoms; or a phenyl or naphthyl radical which is unsubstituted or substituted by halogen, $C_1$–$C_4$-alkyl, $C_1$–$C_4$-alkoxy, nitro, or cyano;
- $X^{(-)}$ is an inorganic anion.

2. The process as claimed in claim 1, wherein said catalyst consists essentially of:
(a) at least 5% of said compound of formula (1), and at least one of the following compounds:
(b) a quaternary ammonium or phosphonium salt of the formula

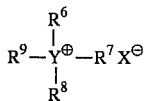 (2)

in which
- $R^6$, $R^7$, $R^8$, and $R^9$ are identical or different and are a linear or branched alkyl radical having 1 to 16 carbon atoms; an unsubstituted phenyl or naphthyl radical; or a phenyl or naphthyl radical substituted by halogen, $C_1$–$C_4$-alkyl, $C_1$–$C_4$-alkoxy, nitro, or cyano; and
- Y is N or P; or (c) an ether which is a crown ether or a polyether of the formula (3)

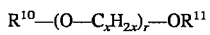 (3), in which
- $R^{10}$ and $R^{11}$ are identical or different and are hydrogen or a linear or branched alkyl radical having from 1 to 8 carbon atoms
- x is a number from 2 to 6; and
- r is a number from 4 to 14.

3. The process as claimed in claim 2, wherein $X^{(-)}$ in said compound of the formula (1) and in said compound of the formula (2) is fluoride, chloride, bromide, $SO_4^{-2}/2$ or hydrogen sulfate.

4. The process as claimed in claim 1, wherein catalyst compound of formula (1) comprises 20 to 80% by weight of the total catalyst.

5. The process as claimed in claim 2, wherein said catalyst consists essentially of 20 to 80% by weight, of the total catalyst, of the compound of formula (1).

6. The process as claimed in claim 2, wherein said catalyst consists essentially of: 20 to 80% by weight of the compound of formula (1), essentially the balance of said catalyst being said compound of formula (2) and said compound of formula (3).

7. The process as claimed in claim 1, wherein one or two of the radicals $R^1$, $R^2$, and $R^3$ of said formula (1) are alkoxypolyoxyalkyl radicals.

8. The process as claimed in claim 1, wherein one, two, or three chlorine atoms in the compound of formula (4) are replaced by fluorine atoms.

9. The process as claimed in claim 8, wherein the number of said chlorine atoms replaced is one or two.

10. The process as claimed in claim 1, wherein said alkali metal fluoride is potassium fluoride, rubidium fluoride, cesium fluoride, or a mixture thereof.

11. The process as claimed in claim 1, wherein said alkali metal fluoride comprises potassium fluoride.

12. The process as claimed in claim 1, wherein the molar ratio of said catalyst to the compound of formula (4) is equal to or less than 1:8.

13. The process as claimed in claim 2, wherein said molar ratio ranges from 1:10 to 1:50.

14. The process as claimed in claim 1, wherein the process is carried out essentially in the absence of solvent.

15. The process as claimed in claim 1, wherein said reaction temperature is in the range of 90° to 180° C.

16. The process as claimed in claim 15, wherein said reaction temperatures is in the range of 120° to 170° C.

17. The process as claimed in claim 1, wherein said compound of formula (4) is 2-chlorobenzonitrile, 4-chlorobenzonitrile, 2,3-dichlorobenzonitrile, 3,4-dichlorobenzonitrile, 2,5-dichlorobenzonitrile, 4-chloro-3-fluorobenzonitrile, 2-chloro-5-fluorobenzonitrile, 2,4-dichlorobenzonitile, 2,6-dichlorobenzonitrile, 2,4-dichloro-3-fluorobenzonitrile, 2,4-dichloro-5-fluorobenzonitrile; 2,4,5-trichlorobenzonitrile, 2,3,4-trichlorobenzonitrile, 2,3,4-trichloro-5-fluorobenzonitrile or 2,4,5-trichloro-3-fluorobenzonitrile.

18. The process as claimed in claim 1, wherein the yield of the product of said process is at least 15%.

* * * * *

UNITED STATES PATENT AND TRADEMARK OFFICE
CERTIFICATE OF CORRECTION

PATENT NO. : 5,466,859
DATED : November 14, 1995
INVENTOR(S) : Thomas Schach, Theodor Papenfuhs and Ralf Pfirmann It is certified that error appears in the above-indentified patent and that said Letters Patent is hereby corrected as shown below:

In claim 1, at column 7, line 17, please insert --of an-- after "weight" and before "aprotic".

In claim 3, at column 8, line 14, the formula "$SO_4^{-2}/2$" should read --$SO_4^{2-}/_2$--.

In claim 13 at column 8, line 43 "claim 2" should read --claim 12--.

In claim 16, at column 8, line 50, "temperatures" should read --temperature--.

In claim 17 at column 8, lines 55-56, "2,4-dichlorobenzo-nitile" should read --2,4-dichlorobenzonitrile-- .

Signed and Sealed this

Fourth Day of June, 1996

*Attest:*

BRUCE LEHMAN

*Attesting Officer*    *Commissioner of Patents and Trademarks*